US009066904B2

(12) United States Patent
Young

(10) Patent No.: US 9,066,904 B2
(45) Date of Patent: Jun. 30, 2015

(54) COMPOSITION CONTAINING AN ESSENTIAL OIL PRODUCT AND METHOD FOR USING SUCH TO MAINTAIN NORMAL LEVELS OF TESTOSTERONE

(71) Applicant: Young Living Essential Oils, LC, Lehi, UT (US)

(72) Inventor: D. Gary Young, Alpine, UT (US)

(73) Assignee: Young Living Essential Oils, LC, Lehi, UT (US)

( * ) Notice: Subject to any disclaimer, the term of this patent is extended or adjusted under 35 U.S.C. 154(b) by 0 days.

(21) Appl. No.: 14/080,679

(22) Filed: Nov. 14, 2013

(65) Prior Publication Data

US 2014/0271957 A1 Sep. 18, 2014

Related U.S. Application Data

(60) Provisional application No. 61/790,031, filed on Mar. 15, 2013, provisional application No. 61/725,549, filed on Nov. 13, 2012.

(51) Int. Cl.
*A61K 36/00* (2006.01)
*A61K 36/15* (2006.01)
*A61K 45/06* (2006.01)
*A61K 9/00* (2006.01)

(52) U.S. Cl.
CPC .............. *A61K 36/15* (2013.01); *A61K 45/06* (2013.01); *A61K 9/0014* (2013.01); *A61K 2236/00* (2013.01)

(58) Field of Classification Search
CPC ............................ A61K 36/00; A61K 36/15
USPC ......................................... 424/770, 725, 775
See application file for complete search history.

(56) References Cited

U.S. PATENT DOCUMENTS

| 5,665,386 A | 9/1997 | Benet et al. |
| 6,187,811 B1 * | 2/2001 | Lane ............................ 514/458 |
| 2006/0018937 A1 | 1/2006 | Friedman et al. |
| 2009/0169487 A1 | 7/2009 | Hedayat |

FOREIGN PATENT DOCUMENTS

| JP | 74006918 B * | 2/1974 |
| JP | H07258101 | 10/1995 |
| JP | H2010051591 A | 3/2011 |
| WO | 01/91589 A | 12/2001 |

OTHER PUBLICATIONS

Kaiser C.S. et al, "Pharmaceutical Applications of Supercritical Carbon Dioxide," Die Pharmazie, Govie Verlag Pharmazeutishcer Verlag GMBH, Jan. 1, 2001, pp. 907-926, vol. 56, No. 12, XP001525673, ISSN: 0031-7144, Table 2, Eschborn, DE.
International Search Report and Written Opinion of the International Searching Authority from related PCTUS2013/070186, Nov. 2, 2014.

\* cited by examiner

*Primary Examiner* — Chris R Tate
*Assistant Examiner* — Deborah Davis
(74) *Attorney, Agent, or Firm* — Bateman IP; Christopher L. Wight

(57) ABSTRACT

A composition useful for maintaining healthy levels of testosterone in men and women. The composition includes essential oils from a tree of the genus *Picea* or a product of this oil. The essential oil product can specifically come from essential oil from the plant *Picea pungens*, commonly referred to as Blue Spruce. Also disclosed is a method for maintaining healthy levels of testosterone in men and women utilizing the composition. In some implementations, the composition is a pharmaceutical composition that further includes a penetration enhancer. A method for utilizing the pharmaceutical composition for treating hypogonadism is also disclosed.

24 Claims, No Drawings

COMPOSITION CONTAINING AN ESSENTIAL OIL PRODUCT AND METHOD FOR USING SUCH TO MAINTAIN NORMAL LEVELS OF TESTOSTERONE

BACKGROUND

One aspect of the invention relates to essential oils. Essential oils are natural and aromatic liquids found in the roots, stems, bark, seeds, flowers, and other parts of plants. Technically, essential oils are fat soluble, non-water-based phytochemicals that include volatile organic compounds. The chemistry of any particular essential oil can be very complex and may consist of hundreds of different and unique chemical compounds. These oils give plants their distinctive smells, provide protection against disease, and assist in pollination. In their pure form, essential oils are translucent with colors ranging from clear to pink to blue.

Essential oils are used in hygiene and personal care products, for adding flavor to food and drink, and for adding scents to perfumes and cleaning products. At different times throughout history, essential oils have also been used for medical purposes in which these oils are inhaled, applied topically, or ingested. The present invention provides an essential oil composition containing an essential oil product, and a method of using the composition.

Another aspect of the invention relates to testosterone levels. Testosterone is the major circulating androgen in men. More than 95% of the 6-7 mg of testosterone produced per day is secreted by the approximately 500 million Leydig cells in the testes. Two hormones produced by the pituitary gland, luteinizing hormone ("LH") and follicle stimulating hormone ("FSH"), are required for the development and maintenance of testicular function.

The most important hormone for the regulation of Leydig cell number and function is LH. In eugonadal men, LH secretion from the pituitary is inhibited through a negative-feedback pathway by increased concentrations of testosterone through the inhibition of the release of gonadotropin-releasing hormone ("GRH") by the hypothalamus. FSH promotes spermatogenesis and is essential for the normal maturation of sperm. FSH secretion from the pituitary normally is inhibited through a negative-feedback pathway by increased testosterone concentrations.

Testosterone is responsible primarily for the development and maintenance of secondary sex characteristics in men. In the body, circulating testosterone is metabolized to various 17-keto steroids through two different pathways. Testosterone can be metabolized to dihydrotestosterone ("DHT") by the enzyme 5α-reductase. There are two forms of 5α-reductase in the body: one form is found predominately in the liver and non-genital skin while another form is found in the urogenital tract of the male and the genital skin of both sexes. Testosterone can also be metabolized to estradiol ("$E_2$") by an aromatase enzyme complex found in the liver, fat, and the testes.

Testosterone circulates in the blood 98% bound to protein. In men, approximately 40% of the binding is to the high-affinity sex hormone binding globulin ("SHBG"). The remaining 60% is bound weakly to albumin. Thus, a number of measurements for testosterone are available from clinical laboratories. The term "free" testosterone as used herein refers to the fraction of testosterone in the blood that is not bound to protein. The term "total testosterone" or "testosterone" as used herein means the free testosterone plus protein-bound testosterone. The term "bioavailable testosterone" as used herein refers to the non-SHBG bound testosterone and includes testosterone weakly bound to albumin.

The conversion of testosterone to DHT is important in many respects. For example, DHT binds with greater affinity to SHBG than does testosterone. In addition, in many tissues, the activity of testosterone depends on the reduction to DHT, which binds to cytosol receptor proteins. The steroid-receptor complex is then transported to the nucleus where it initiates transcription and cellular changes related to androgen action. DHT is also thought to lower prostate volume and inhibit tumor development in the prostate. Thus, given the importance of DHT and testosterone in normal body functioning, researchers frequently assess and report androgen concentrations in patients as total androgen ("DHT+T") or as a ratio of DHT to testosterone ("DHT/T ratio").

The UCLA-Harbor Medical Center indicates that the normal total testosterone levels in adult men range from 298 to 1043 ng/dL, with normal free testosterone levels ranging from 3.5 to 17.9 ng/dL.

There is considerable variation in the half-life of testosterone reported in the literature, ranging from 10 to 100 minutes. Researchers do agree, however, that circulating testosterone has a diurnal variation in normal young men. Maximum levels occur at approximately 6:00 to 8:00 a.m. with levels declining throughout the day. Characteristic profiles have a maximum testosterone level of 720 ng/dL and a minimum level of 430 ng/dL. The physiological significance of this diurnal cycle, if any, however, is not clear.

Male hypogonadism results from a variety of patho-physiological conditions in which testosterone concentration is diminished below the normal range. The hypogonadic condition is sometimes linked with a number of physiological changes, such as diminished interest in sex, impotence, reduced lean body mass, decreased bone density, and lowered mood and energy levels.

Researchers generally classify hypogonadism into one of three types. Primary hypogonadism includes the testicular failure due to congenital or acquired anorchia, XYY Syndrome, XX males, Noonan's Syndrome, gonadal dysgenesis, Leydig cell tumors, maldescended testes, varicocele, Sertoli-Cell-Only Syndrome, cryptorchidism, bilateral torsion, vanishing testis syndrome, orchiectomy, Klinefelter's Syndrome, chemotherapy, toxic damage from alcohol or heavy metals, and general disease (renal failure, liver cirrhosis, diabetes, myotonia dystrophica). Patients with primary hypogonadism show an intact feedback mechanism in that the low serum testosterone concentrations are associated with high FSH and LH concentrations. However, because of testicular or other failures, the high LH concentrations are not effective at stimulating testosterone production.

Secondary hypogonadism involves an idiopathic gonadotropin or LH-releasing hormone deficiency. This type of hypogonadism includes Kallman's Syndrome, Prader-Labhart-Willi's Syndrome, Laurence-Moon-Biedl's Syndrome, pituitary insufficiency/adenomas, Pasqualini's Syndrome, hemochromatosis, hyperprolactinemia, or pituitary-hypothalamic injury from tumors, trauma, radiation, or obesity. Because patients with secondary hypogonadism do not demonstrate an intact feedback pathway, the lower testosterone concentrations are not associated with increased LH or FSH levels. Thus, these men have low testosterone serum levels but have gonadotropins in the normal to low range.

Third, hypogonadism may be age-related. Men experience a slow but continuous decline in average serum testosterone after approximately age 20 to 30 years. Researchers estimate that the decline is about 1-2% per year. Cross-sectional studies in men have found that the mean testosterone value at age 80 years is approximately 75%, of that at age 30 years. Because the serum concentration of SHBG increases as men age, the fall in bioavailable and free testosterone is even greater than the fall in total testosterone. Researchers have estimated that approximately 50% of healthy men between the ages of 50 and 70 have levels of bioavailable testosterone that are below the lower normal limit. Moreover, as men age, the circadian rhythm of testosterone concentration is often muted, dampened, or completely lost. The major problem with aging appears to be within the hypothalamic-pituitary unit. For example, researchers have found that with aging, LH levels do not increase despite the low testosterone levels. Regardless of the cause, these untreated testosterone deficiencies in older men may lead to a variety of physiological changes, including sexual dysfunction, decreased libido, loss of muscle mass, decreased bone density, depressed mood, and decreased cognitive function. The net result is geriatric hypogonadism, or what is commonly referred to as "male menopause."

Today, hypogonadism is the most common hormone deficiency in men, affecting about 5 in every 1,000 men. At present, it is estimated that only five percent of the estimated four to five million American men of all ages with hypogonadism currently receive testosterone replacement therapy. Thus, for years, researchers have investigated methods of delivering testosterone to men. Current testosterone methods for treating hypogonadism suffer from one or more drawbacks.

The present invention is directed to compositions and methods that are useful for maintaining healthy testosterone levels and pharmaceutical compositions and methods for treating hypogonadism.

SUMMARY

The present invention relates to essential oils and the use of compositions containing an essential oil product to increase health and wellness in humans. Specifically, the invention relates to compositions useful for maintaining healthy testosterone levels in men and women. In some embodiments, the compositions include essential oils from a tree of the genus *Picea* or a product of this oil. In other embodiments, compositions include essential oils from a tree of the genus *Pinus* or a product of this oil. The essential oil or essential oil product can specifically come from essential oil from the plant *Picea pungens*, commonly referred to as Blue Spruce. The invention also relates to methods for maintaining healthy levels of testosterone in men and women utilizing the compositions.

In some implementations, the compositions comprise a pharmaceutical composition that further includes a penetration enhancer. The invention may thus further include a method for utilizing the pharmaceutical composition for treating hypogonadism.

DETAILED DESCRIPTION OF EXEMPLARY EMBODIMENTS

This specification describes exemplary embodiments and applications of the invention. The invention, however, is not limited to these exemplary embodiments and applications or to the manner in which the exemplary embodiments and applications operate or are described herein. Moreover, the singular forms "a," "an," and "the" include plural referents unless the context clearly dictates otherwise. Thus, for example, reference to a surface includes reference to one or more surfaces. In addition, where reference is made to a list of elements (e.g., elements a, b, and c), such reference is intended to include any one of the listed elements by itself, any combination of less than all of the listed elements, and/or a combination of all of the listed elements.

The present invention relates to essential oils and the use of compositions containing an essential oil product to increase health and wellness in humans. Specifically, the invention relates to compositions useful for maintaining healthy testosterone levels in men and women. The compositions include essential oils from a tree of the genus *Picea* or a product of this oil (collectively referred to herein as an "essential oil product"). The essential oil or essential oil product can specifically come from essential oil from the plant *Picea pungens*, commonly referred to as Blue Spruce. Alternatively, the essential oil or essential oil product can specifically come from essential oil from the plant *Pinus monophylla*, commonly referred to as Pinyon Pine. The invention also relates to a method for maintaining healthy levels of testosterone in men and women utilizing the composition.

In some implementations, the compositions comprise a pharmaceutical composition that further includes a penetration enhancer. The invention may thus further include methods for utilizing the pharmaceutical compositions for treating hypogonadism.

*Picea pungens*

In some aspects, the present invention relates to compositions comprising essential oil derived from a tree of the genus *Picea*. *Picea* is a genus of coniferous evergreen trees found in the northern temperate and boreal regions of the earth. This genus includes the following species Brewer's Spruce (*Picea breweriana*), Sitka Spruce (*Picea sitchensis*), Engelmann Spruce (*Picea engelmannii*), White Spruce (*Picea glauca*), Sargent's Spruce (*Piceas brachytyla*), Chihuahua Spruce (*Picease chihuahuana*), Burmese Spruce (*Picea farrerri*), Likiang Spruce (*Picea likiangensis*), Martinez Spruce (*Picea martinezii*), Taiwan Spruce (*Picea morrissonicola*), Veitch's Spruce (*Picea neoveichii*), Oriental Spruce (*Picea orientalis*), Purple Spruce (*Picea purpurea*), Schrenk's Spruce (*Piceas shrenkiana*), Morina Spruce (*Picea smithiana*), Sikkim Spruce (*Picea spinulosa*), Tiger-tail Spruce (*Picea torano*), Wilson's Spruce (*Picea wilsonii*), Norway Spruce (*Picea abies*), Alcock's Spruce (*Picea alcoquiana*), Alpine Spruce (*Picea alcoquiana*), Dragon Spruce (*Picea asperata*), *Picea crassifolia*, Glehn's Spruce (*Picea glehnii*), Jezo Spruce (*Picea jexoensis*), Korean Spruce (*Piceas koraiensis*), Koyama's Spruce (*Picea koyamae*), Black Spruce (*Picea mariana*), Meyer's Spruce (*Picea meyeri*), Siberian Spruce (*Picea obovata*), Serbian Spruce (*Picea omorika*), Blue Spruce or Colorado spruce (*Picea pungens*), *Picea retroflexa*, and Red Spruce (*Picea rubens*). These trees grow to about 60 to about 200 feet tall when mature, and can be distinguished by their whorled branches and conical form. The needles of the tree are attached to the branches in a spiral fashion. The needles are shed when the tree is four to ten years old, leaving rough branches.

One species of the *Picea* genus is the *Picea pungens*, which is also called Colorado blue spruce, Blue Spruce, or Idaho Blue Spruce (herein "Blue Spruce"). Blue Spruce is a tree that is primarily native to the central and southern United States Rocky Mountains. It is commonly planted as an ornamental tree due to symmetry and color. Blue spruce typically has brittle knotty wood and is not important for timber wood.

Blue Spruce is a medium-sized coniferous evergreen tree that generally grows to 100 feet tall and has a trunk diameter of up to 5 feet. The bark is thin and gray, with narrow vertical furrows. The crown is conic in young trees, becoming cylindric in older trees. The shoots are stout, orange-brown, usually glabrous, and with prominent pulvini.

The leaves of the Blue Spruce are 1.5 to 2 inches long, dagger shaped, sharply mucronate, lanceolate, sessile, acuminate, deflexed, rigid, coriaceous, somewhat serrulate, very numerous, bright green above and slightly glacous below. The leaves are needle-like, 15-30 millimeters (0.59-1.2 in) long, stout, rhombic in cross-section, dull gray-green to bright glaucous blue, with several lines of stomata; the tip is viciously sharp.

The cones of the Blue Spruce are pendulous, slender cylindrical, 6-11 cm (2.4-4.3 in) long and 2 cm (0.79 in) broad when closed, opening to 4 cm (1.6 in) broad. They have thin, flexible scales 20-24 mm (0.79-0.94 in) long, with a wavy margin. They are reddish to violet, maturing pale brown 5-7 months after pollination. The seeds are black, 3-4 mm (0.12-0.16 in) long, with a slender, 10-13 mm (0.39-0.51 in) long pale brown wing.

Essential Oil Production from *Picea pungens*

Essential oils from a tree of the genus *Picea* can be distilled acquired from the entire plant. Specifically, the trunk, branches, leaves, seeds, and bark can be distilled. In some instances, the roots may be distilled as well. Use of all parts of the tree can not only provide good oil yields but is eco-friendly, reducing waste.

After these trees are harvested their essential oils may be extracted using various techniques including distillation, $CO_2$ extraction, or solvent extraction. Specifically, the essential oils may be extracted using a steam distillation technique. Three methods of steam distillation can be used to extract essential oil from plant material of these trees, including simple distillation, hydro-distillation, and traditional distillation.

In simple distillation, the plant material is loaded into the extraction chamber filled with water, which is heated to soften the plant fiber so that the oil molecules can be released. As steam begins to rise, the oil molecules are released as vapors, which are carried with the steam into the condenser. The cooling water in the condenser converts the steam to water and the vapors to oil. The oil and water mixture continues to flow into the separator where the oil rises to the top of the water so that it can be drained off into containers.

In hydro distillation, plant material is immersed in boiling water that is in constant motion while steam is injected into the chamber. The gas is then released into the steam, which carries it to the condenser where the steam and vapor are gradually cooled to a liquefied form. The water and oil mixture travels into the separator so that the oil can flow to the top of the water and be poured off into containers.

In traditional distillation, plant material is loaded into the extraction chamber and tightly compacted. As the boiler heats the water, steam is released into the bottom of the chamber and starts to travel upward, saturating the material. The steam impregnates the plant fiber, causing it to release the oil molecule as a gas from the molecule pocket or channel. Then the steam carries the gas to the condenser where it goes through a phase-change condensation as it passes through the cooling process in the swan neck and liquefies into water and oil. The water and oil mixture then flows into the separator where the oil can rise to the top of the water to be poured off into containers.

In each of these processes as the steam rises, it carries the released oil vapor into the condenser where the water and oil vapor convert to a liquid and flow into the separator so that the oil can rise to the top of the water and be drained off. The essential oil may be collected together or in fractions. The resulting essential oil can be approximately 100% pure, uncut essential oil. The oil generally includes a pink florescent color and has a pleasant, woody aroma.

Analysis of Blue Spruce Essential Oil

The table shown as Table 1 presents the result of a gas chromatograph (GC) analysis of a sample of blue spruce essential oil.

TABLE 1

| Components | (Approximate) Percentage of Total |
|---|---|
| Alpha-Pinene | 23.79 |
| Limonene* | 22.52 |
| Beta-Pinene | 8.75 |
| Camphene | 7.37 |
| Bornyl Acetate | 6.65 |
| Delta-3-Carene | 6.44 |
| Myrcene | 5.13 |
| Camphor | 4.75 |
| Terpinolene | 2.04 |
| Exo-Methyl-Camphenilol | 1.58 |
| Borneol | 1.48 |
| Sabinene | 1.41 |
| Tricyclene | 1.21 |
| Alpha-Thujene | 1.21 |

As shown in Example 1, blue spruce essential oil contains high percentages of alpha-pinene and limonene, as well as containing diterpenes and several other compounds. It is noted that the presence of diterpenes in conifer trees is not well classified. Moreover, blue spruce essential oil is high in the constituents Cembrene and Cembrenol, which is not typical of conifers.

Moreover, while not specifically distinguishable or identified in the GC analysis, Blue spruce essential oil appears to include one or more active ingredients that aids in the production of testosterone in humans. Further testing may be required to identify the active ingredients in the Blue Spruce essential oil.

Uses of Blue Spruce Essential Oil

Some embodiments of the present invention are directed to a therapeutic composition for percutaneous administration comprising one or more essential oil or product derived from one or more essential oils, which may be collectively referred to as the "essential oil product." The essential oils can include an essential oil from a plant of the genus *Picea*. For example, pure essential oil from a plant of the genus *Picea* can be included in the composition. In another example, a portion of an essential oil from a plant of the genus *Picea* can be included in the composition. The product derived from the one or more essential oil can be separated from, concentrated from, or otherwise derived from the essential oil.

Specifically, an essential oil product can include an essential oil of blue spruce that is concentrated down to concentrate the active ingredients in the oil. The oil can be concentrated down to various concentration ratios, such as 2:1, 3:1, 5:1, 10:1, 15:1, 20:1, etc. Such concentration can be accomplished using any suitable evaporator, such as a centrifugal evaporator, rotary evaporator, or other solvent evaporate (e.g., the Rocket™ evaporator from Dionex Corporation of Sunnyvale, Calif.).

The amount of the essential oils product incorporated in the compositions can vary depending on the particular essential oil product, the desired therapeutic effect, and the time span for which the composition is to provide the therapeutic effect. The compositions are used in a pharmacologically effective amount. This means that the concentration of the essential oil product is such that in the compositions it results in a therapeutic level of active ingredient delivered over the term that a particular composition is used. Such delivery is dependent on a number of variables including the active ingredients in the essential oil product, the form of the concentration, the time period for which the individual dosage unit is to be used, the flux rate of the essential oil product in the composition, and the surface area of application site. The amount of the essential oil product in the composition can be experimentally determined based on the flux rate of the essential oil product through the composition, and through the skin when used with and without enhancers. In some embodiments, the composition is applied to the skin in an amount sufficient to increase free testosterone by greater than about 10%, 15%, or 20%. In other embodiments, the composition is applied to the skin in an amount sufficient to increase total testosterone by greater than about 15%, 20%, or 25%.

Essential oil product(s) within the composition can range from 1% to 100% included all values and sub-ranges therein. For example, a composition may include up to 5%, 10%, 15%, 20%, 25%, 30%, 35%, 40%, 45%, 50%, 55%, 60%, 70%, 75%, 80%, 85%, 90%, 95%, or 100% of essential oil product.

In some embodiments, the compositions comprise a penetration enhancer. The penetration enhancer is an agent that accelerates the delivery of the essential oil product through the skin. This agent can include accelerants, adjuvants, and absorption promoters, and can be collectively referred to herein as enhancers. This class of agents includes those with diverse mechanisms of action including those which have the function of improving the solubility and diffusibility of the essential oil product, and those which improve percutaneous absorption or by changing the ability of the stratum corneum to retain moisture, softening the skin, improving the skin's permeability, acting as penetration assistants or hair follicle openers or changing the state of the skin such as a boundary layer.

The penetration enhancer of the present invention can be an additional essential oil or blend of essential oils. Specifically, the additional essential oil(s) can include oils capable of accelerating the delivery of the essential oil product through the skin. Some such oils include oils high in their concentration of monoterpenes and/or sequeterpines, including frankincense, bergamot, rosewood, orange, coriander, lemon, and others. In one embodiment, the essential oil penetration enhancer is comprised of one or more of the following substances: blue spruce essential oil, coriander essential oil, davana essential oil, lavender essential oil, ocotea essential oil, cedarwood essential oil, hinoki essential oil, and lemon essential oil.

A penetration enhancer within the composition can range from 1% to 100% including all values and sub-ranges therein. For example, a composition may include up to 5%, 10%, 15%, 20%, 25%, 30%, 35%, 40%, 45%, 50%, 55%, 60%, 70%, 75%, 80%, 85%, 90%, 95%, or 100% of penetrating enhancer.

The composition may be used in a final dosage form which may be any of the following: a solid or semi-solid disc or patch formed by moulding, cutting, punching or slicing of the mixture, a cream, a mucilage, a gel, a paste, a jelly, an ointment.

Although the examples of use of the composition involve human men and women, the composition and method of the present invention may be used to treat these disorders in humans and animals of any kind, such as dogs, pigs, sheep, horses, cows, cats, zoo animals, commercially bred farm animals, and the like.

Through detailed clinical experiments, it has been found that Blue Spruce essential oil is capable of increasing blood testosterone levels in men and women. Embodiments of the present invention are further illustrated by the following examples, which should not be construed as limiting in any way. These examples are not meant to be limiting in any way as one ordinarily skilled in the art will recognize other various parameters and control groups that may be used to carry out the intended function of the present invention as intended herein. The practice of the present invention will employ, unless otherwise indicated, conventional techniques of pharmacology and pharmaceutics, which are within the skill of the art.

EXAMPLES

Example 1

As stated above Blue Spruce essential oil has an effect of increasing blood testosterone levels in the body. Specifically, Blue Spruce essential oil has the effect of increasing blood testosterone levels in men.

In this example, three males of varying age (19-68) were recruited in a health center in the United States. The patients all had total testosterone levels of less than 350 ng/dL, and each had previously been diagnosed to have these lower levels due to a lack of appropriate production of luteinizing hormone. A free and total testosterone level was obtained by blood drawing and then lab run via liquid chromatography—mass spectrometry—preparative LC-MS. This is the same lab machine used for fast and mass directed purification of natural-products extracts and new molecular entities important to food, pharmaceutical, agrochemical and other industries.

The volunteers were then given *Picea pungens* Blue Spruce essential oil from Young Living Essential Oils, LC, which was extracted from entire Blue Spruce trees grown in Idaho, USA via steam distillation. This essential oil was 100% pure and uncut. The volunteers were advised to topically apply 8 drops of oils on the chest or testicles every day after showering. The volunteers were advised to continue this routine for 14 days. They were also advised not to change or add any other supplement or nutraceutical and to not change their diet.

Immediately after the 14 days trial period, another blood draw was conducted on each of the volunteers and was tested for serum free and total testosterone. The levels were then compared to those obtained 14 days before and the percentage change was noted. There were no complications.

The results are shown below.
Volunteer 1
Free Testosterone—Increased 25.5% (4.7 to 5.9 pg/mL)
Total Testosterone—Increased 15.9% (238 to 276 ng/dL)
Volunteer 2
Free Testosterone—Increased 14.5% (8.3 to 9.5 pg/mL)
Total Testosterone—Increased 34.3% (306 to 411 ng/dL)
Volunteer 3
Free Testosterone—Decreased 13.1% (9.2 to 8.4 pg/mL)
Total Testosterone—Increased 30.1% (246 to 320 ng/dL)
Averages
Free Testosterone was increased (on average) 9.0%
Total Testosterone was increased (on average) 26.8%

Example 2

As stated above, Blue Spruce essential oil also has the effect of increasing blood testosterone levels in women. Another experiment was run using the same methods explained in Example 1, but with a female volunteer. After 14 days of topically applying the Blue Spruce essential oil, this female volunteer's blood serum testosterone levels had increased relative to those measured before the 14 day trial.

Specifically, her total testosterone increased approximately 60% and her free testosterone increased 27%.

The results of these experiments are as follows. The topical application of eight drops of Blue Spruce essential oil to men increased, on average, their total and free blood testosterone levels. Also, the application of eight drops of Blue Spruce essential oil to a woman increased her total and free blood testosterone levels.

Although specific embodiments and applications of the invention have been described in this specification, these embodiments and applications are exemplary only, and many variations are possible.

I claim:

1. A method of increasing testosterone levels in humans having low testosterone, the method comprising administering to a human having low testosterone a composition containing an effective amount of an essential oil from a plant of *Picea pungens*.

2. The method of claim 1, wherein administering comprises topically applying the composition to the skin.

3. The method of claim 2, wherein topically applying the composition comprises at least one of spraying on the composition, rubbing on the composition, and combinations thereof.

4. The method of claim 2, wherein topically applying the composition comprises topically applying one or more drops of the composition on the skin daily for two or more days.

5. The method of claim 4, wherein topically applying the composition comprises topically applying three or more drops of the composition on the skin daily for two or more days.

6. The method of claim 4, wherein topically applying the composition comprises topically applying six or more drops of the composition on the skin daily for two or more days.

7. The method of claim 4, wherein topically applying the composition comprises topically applying eight or more drops of the composition on the skin daily for two or more days.

8. The method of claim 4, wherein topically applying the composition comprises topically applying one or more drops of the composition on the skin daily for five or more days.

9. The method of claim 4, wherein topically applying comprises topically applying six or more drops of the composition on the skin daily for five or more days.

10. The method of claim 4, wherein the composition is applied to the skin in an amount sufficient to increase free testosterone by greater than about 10%.

11. The method of claim 4, wherein the composition is applied to the skin in an amount sufficient to increase free testosterone by greater than about 15%.

12. The method of claim 4, wherein the composition is applied to the skin in an amount sufficient to increase free testosterone by greater than about 20%.

13. The method of claim 4, wherein the composition is applied to the skin in an amount sufficient to increase total testosterone by greater than about 15%.

14. The method of claim 4, wherein the composition is applied to the skin in an amount sufficient to increase total testosterone by greater than about 20%.

15. The method of claim 4, wherein the composition is applied to the skin in an amount sufficient to increase total testosterone by greater than about 25%.

16. The method of claim 1, wherein the composition comprises at least 5% essential oil from a tree of *Picea pungens*.

17. The method of claim 1, wherein the composition comprises at least 25% essential oil from a tree of *Picea pungens*.

18. The method of claim 1, wherein the composition comprises at least 50% essential oil from a tree of *Picea pungens*.

19. The method of claim 1, wherein the composition comprises at least 75% essential oil from a tree of *Picea pungens*.

20. The method of claim 1, wherein the composition further comprises one or more of an additional essential oil, a carrier oil, and a lotion.

21. A method for the treatment of hypogonadism where the disease is characterised by low levels of testosterone in the blood, which comprises administering to a patient in need thereof a medicament containing an effective amount of an essential oil from *Picea pungens*, said medicament being effective to achieve therapeutically effective increases in testosterone in the blood levels when administered on a once- or twice-daily basis.

22. The method of claim 21, wherein the hypogonadism is characterised by levels of testosterone in the blood lower than 300 ng/dL.

23. The method of claim 21, wherein the medicament is administered in an amount sufficient to increase free testosterone by an amount greater than about 10%.

24. The method of claim 21, wherein the medicament is administered in an amount sufficient to increase total testosterone by an amount greater than about 15%.

* * * * *